United States Patent [19]

Huber

[11] Patent Number: 5,045,476
[45] Date of Patent: Sep. 3, 1991

[54] METHOD AND DEVICE FOR ANALYZING SOLID SUBSTANCES ON MERCURY

[75] Inventor: Bernhard Huber, Überlingen, Fed. Rep. of Germany

[73] Assignee: Bodenseewerk Perkin Elmer GmbH, Überlingen, Fed. Rep. of Germany

[21] Appl. No.: 527,926

[22] Filed: May 24, 1990

[30] Foreign Application Priority Data

Jun. 10, 1989 [DE] Fed. Rep. of Germany ....... 3919042

[51] Int. Cl.$^5$ ............................................. G01N 21/00
[52] U.S. Cl. ....................................... 436/81; 422/64; 422/78; 422/80; 422/82.09; 422/83; 436/155; 436/177; 436/178; 436/181; 436/182; 356/36; 356/437
[58] Field of Search ................. 436/81, 155, 177, 178, 436/181, 82; 422/64, 78, 80, 82.09, 83; 356/36, 437

[56] References Cited

U.S. PATENT DOCUMENTS

| 4,208,372 | 6/1980 | Huber | 422/65 |
|---|---|---|---|
| 4,294,126 | 10/1981 | Ohkawa | 73/864.21 |
| 4,443,105 | 4/1984 | Huber | 356/312 |
| 4,455,280 | 6/1984 | Shinohara | 422/63 |

FOREIGN PATENT DOCUMENTS 3704533 8/1988 Fed. Rep. of Germany .

OTHER PUBLICATIONS

Monthey, G. et al., "Die Bestimmung von Quecksilber in Subnamo-Bis Mikorgramm Bereich Mittels Hammlaser Atom-Absorptionsspektral-Photometric Nach Vorheriger Amalgamerung on Edelmetall".
Wissenschaftliche Zestschmift der Wilhelm Pieck-Umversität Rostock, Math-Naturwiss. Reihe 1978, 27(6), S 643-650.
Muscat, V. I. et al., "Simple and Versatile Atomic Fluroescence System for Determination of Nanogram Quantities of Mercury". Anal. Chem., vol. 44, No. 2, Feb. 1972.
Welz, Bernhard et al., "Cold Vapor Atomic Absorption Spectometric Determination of Mercury Using Sodium Tetrahydroborate Reduction and Collection on Gold", Fresnius Z. Anal. Chem. (1988), 331:324-32.
Kunert, I. et al. "Determination of Mercury by Atomic Absorption Spectrometry with Cold Vapour and Electrothermal Techniques", Analytica Chimica Acta. 106, 1979, S.285-297.
Neske, P. et al., "Zur Bestemmung von Quecksilber in Wassorn in pp. Bereich", Fresanius Z. Anal. Chem. 1984, 318 S.498-501.
Selmer, F. et al., "Quecksilber in der Troposphore", Ber. Bunsenges. Phys. Chem. 82, 1978, S.1142-1146.

Primary Examiner—David L. Lacey
Assistant Examiner—David Redding
Attorney, Agent, or Firm—Thomas P. Murphy; Edwin T. Grimes

[57] ABSTRACT

For analyzing solid substances on mercury by measuring the atomic absorption, the substance is heated in order to expel the mercury. The generated mercury vapor is conveyed with a carrier gas flow over a body having a large surface made of an amalgam-generating material, so that the mercury vapor bonds and is accumulated as amalgam on the surface of this body. Subsequently, the body is heated in order to set the mercury accumulated as amalgam free again, and is conveyed by a carrier gas flow into a measuring vessel of an atomic absorption spectrometer. The solid substance which is to be analyzed is enclosed within a vessel having a closure which is destroyed during the heating of the solid substance. For this purpose, a cover is sealingly placed onto the vessel above the destructable closure through which cover a carrier gas flow can be supplied and be carried off. Subsequently, the heating of the solid substance takes place with the closure being destroyed, and then the generated mercury vapor being passed by the carrier gas flow over the amalgam-generating body.

11 Claims, 1 Drawing Sheet

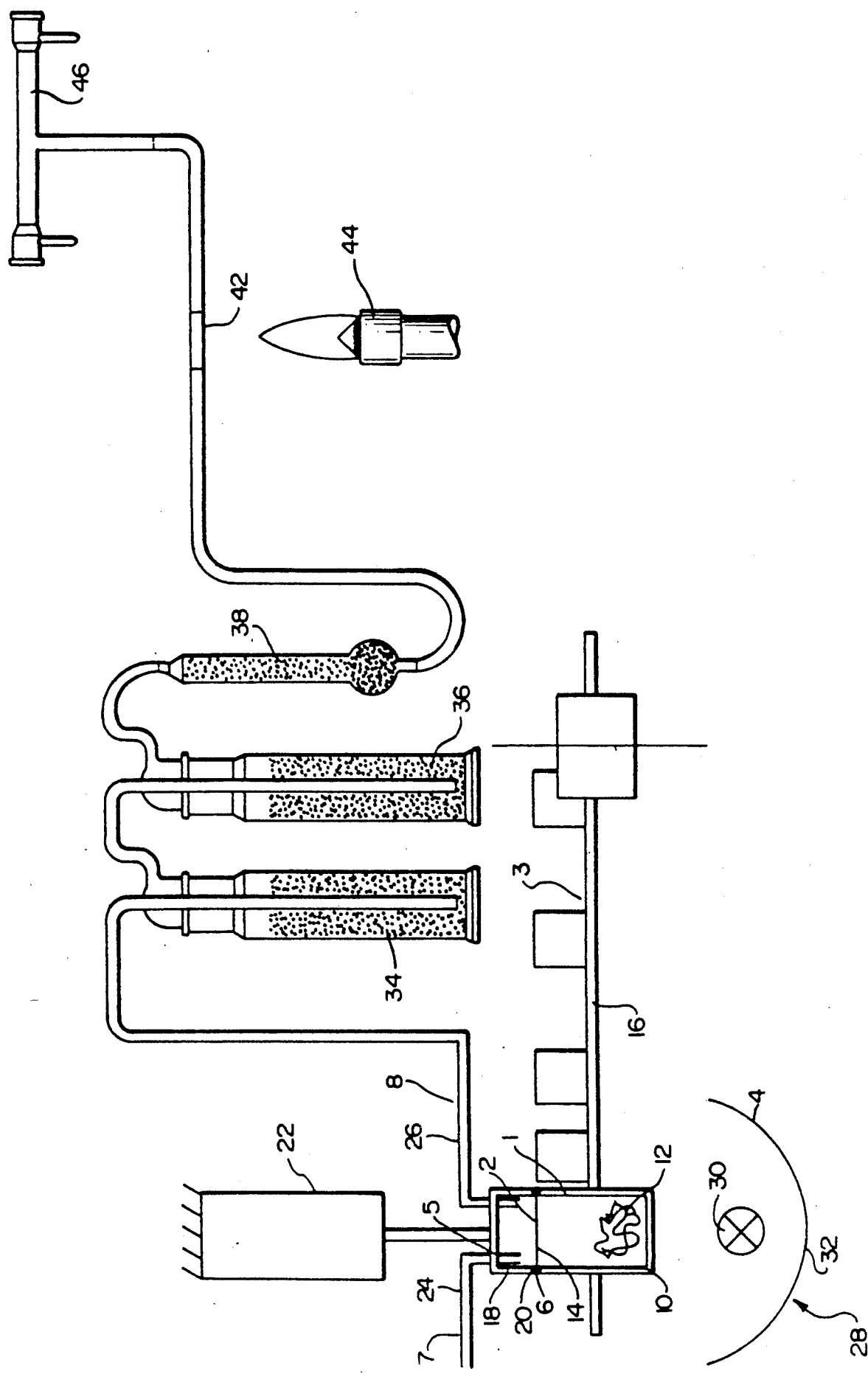

METHOD AND DEVICE FOR ANALYZING SOLID SUBSTANCES ON MERCURY

TECHNICAL FIELD

The invention relates to a method for analyzing solid substances on mercury by measuring the atomic absorption. The invention also relates to a device for the automatic carrying out of such a method.

Usually, solid samples are disintegrated, i.e., dissolved with a strong acid. When mercury is analyzed, this sample solution is mixed with a reagent. Thereby, the mercury is set free as volatile mercury vapor. This mercury vapor is conveyed by a carrier gas flow into a measuring vessel. In the measuring vessel, the concentration of mercury is determined from the atomic absorption. With the volatile mercury, there is the danger that, in treating the sample substance, a portion of the mercury already volatilizes and may escape. In highly sensitive measurements, there can also be contamination by the atmosphere or the reagents. Therefore, the method to which the invention relates operates with solid samples. The mercury is expelled from the solid sample by heating. However, the expulsion of the mercury from the solid sample is not made in a reproducible fashion since the respective, momentary concentration of mercury in the measuring vessel depends on the types of the combinations in which the mercury is present in the sample. Because of this, and in order to increase the sensitivity of the measurement, the mercury is first accumulated as amalgam. From the amalgam, the mercury is set free in a short period of time so that a defined signal peak occurs from which the mercury concentration can be derived.

BACKGROUND ART

By the JP-Z-Eisei Kagaku 29(6), 418–22, it is known to vaporize, for determining mercury in organic samples, the mercury by heating the samples. The mercury is passed through a washing solution and is accumulated as gold amalgam. Then, the gold amalgam is heated and the mercury is set free. The obtained mercury vapor is optically measured. Similar methods for measuring the concentration of mercury in rocks is described in GB-Z "Analyst" (London) 102 (1214), 399–403, and in "Analytica Chimica Acta" 78(2), 479–82.

German Published Patent Application No. 3,641,386 describes a method of automatically generating gaseous or vaporous samples from a liquid for atomic absorption spectroscopy. When carrying out this method, a protective gas is passed over the liquid and, then, a reagent is added to the liquid for forming gaseous or vaporous sample substances. The thus formed sample substances are passed to a trap or a measuring device by means of the protective gas. According to the teaching of German Published Patent Application No. 3,641,386, the entire protective gas is directly passed into the liquid after the reagent addition. Also, different reagents can be consecutively added to the liquid. It is intended to thereby enable faster and more reliable, fully automatic analysis because the protective gas which passes through the liquid has a stirring action. Sample receptacles are successively conveyed to a work station. Thereat, an outlet member is set upon the sample receptacle which is open at the top, by means of a mechanism. This outlet member guides various tubes which are introduced into the sample and contains an outlet communicating with the space above the sample liquid. German Published Patent Application No. 2,748,685 likewise describes an apparatus for producing a gaseous measuring sample from a sample liquid and for passing such measuring sample into a measuring cuvette of an atomic absorption spectrometer by means of a protective gas. Also therein, the sample is arranged on a stepwisely advancing conveyor device. Connections for infeeding and outfeeding the protective gas and for metering the reagent are provided in a connecting member which is vertically movable and can be set upon the sample receptacle by means of a servo motor.

German Published Patent Application No. 2,737,727 describes an apparatus for determining elements in gaseous, solid or liquid samples by using "forward scattering". A measuring light beam having the resonance wavelength of a desired element is passed through a measuring cuvette. A polarizer is arranged in front of the measuring cuvette and an analyzer is located in the rear of the measuring cuvette and arranged crosswise relative to the polarizer. A magnetic field acts upon the measuring cuvette so that the atoms present in the measuring cuvette are subject to the Zeeman effect. The measuring cuvette is connected to a furnace which is closed and contains a crucible holding the sample to be analyzed. By means of a suction device, sample vapor is drawn from the furnace through the measuring cuvette. Due to the interaction with the resonance line components obtained as a result of the Zeeman effect, there is produced a rotation of the polarization plane which is dependent upon the concentration of the desired element and whereby, despite the crosswise arrangement of the polarizer and the analyzer, a light flux passes through the arrangement and which light flux is dependent upon the concentration of the desired element and impinges upon a photoelectric detector.

U.S. Pat. No. 4,023,929 relates to a method of determining the mercury content of water. The water is collected in collecting means, evaporated at 1000° C., and decomposed in a pyrolysis zone at temperatures between 1000° C. and 1200° C. During this operation, mercury vapor is driven passed over a metal surface by means of a carrier gas. The mercury is enriched at the metal surface. The enriched mercury can be driven off again from the adsorbing metal surface by heating and can be measured.

U.S. Pat. No. 4,758,519 describes a method of continuously analyzing gaseous mercury in a gas containing a mercury compound. During this process, the gas is treated with a reducing agent prior to the measurement in order to reduce the mercury compound present in the gas to metallic mercury.

A publication by Mertens and Althaus, entitled "Determination of Mercury with the Aid of the Amalgam Technique Using Hydroxylammonium Chloride and Sodium Borohydride or Tin(II) Chloride", published in "Fresenius Zeitschrift fur analytische Chemie" 1983, vol. 316, pages 696 to 698, describes an apparatus for determining mercury by feeding reagents to a reaction vessel. The thus formed mercury vapor is passed by a nitrogen stream through a wash flash and a drying device and past a gold-platinum net. The mercury is bound thereat as an amalgam and thereby enriched. The gold-platinum net is heated by heating means and the enriched mercury is driven off. The thus recovered mercury vapor is passed into the measuring cuvette of an atomic absorption spectrometer by means of an inert carrier gas like nitrogen. German Published Patent Application No. 3,044,627 relates to an apparatus for introducing a sample into a graphite tube for flameless atomic absorption spectroscopy. A sample is applied to a sample carrier which can be introduced into a crucible shape and is heated by means of a heating device in a contactless manner. The heating device may be formed, for example, as a lamp, the radiation of which is concentrated at the sample by means of a concave mirror. Drying and ashing of the sample thus can be effected outside of the graphite tube. German Patent No. 3,204,584 is concerned with an apparatus for storing a multitude of liquids to be delivered in an automatic chemical analyzer. A movable holder receives a multiple number of closable liquid vessels. This holder conjointly with the liquid vessels is arranged within a chamber. The liquid vessels are individually conveyed to a suction position by means of the holder. An associated closure is provided for each one of the liquid vessels. The closure is opened at the suction position by means of a closure actuating device. A small tube for liquid withdrawal is then introduced into the liquid vessel through an opening in the chamber.

German Patent No. 2,954,181 relates to a sample feeder for automatically feeding a sample from above into a sample infeed opening provided in a furnace for flameless atomic absorption spectroscopy. Sample receptacles are movable into take-up positions by means of a turntable. In the take-up positions, a take-up tube is introduced into the sample receptacle. The sample is taken up and metered into the sample infeed opening of the furnace.

DISCLOSURE OF THE INVENTION

It is the object of the invention to design a method and a device of the type mentioned above so that the danger of a loss of volatile mercury between the sample taking and the analysis and during the analysis is reduced.

Furthermore, it is the object of the invention to design a method of the type mentioned above so that it is easy to automate.

A further object of the invention is to provide an automatic device for the analysis of solid substances on mercury.

The method according to the invention for this purpose provides that the solid substance which is to be analyzed is enclosed within a vessel with a closure which is destroyed during the heating of the solid substance.

Thus, the sample which is to be analyzed is introduced into a vessel without being changed. This vessel is closed until the vessel is heated in the analyzing apparatus in order to expel the mercury. With this heating, the closure is first destroyed. The released mercury cannot get lost. It is accumulated as amalgam and is then determined by the atomic absorption measurement.

About the destructible closure a cover can be sealingly placed on the vessel through which closure a carrier gas flow can be supplied or carried off. Subsequently, the heating of the solid substance is carried out with the closure being destroyed and then the generated mercury vapor being guided by the carrier gas flow over the amalgam-generating body. The heating of the solid substance is made by radiation which is focused onto the substance.

An automation of the method can be achieved in that the samples are consecutively, automatically conveyed to a location where the placement of the cover and the heating is made.

After introducing the substance which is to be analyzed, the vessel can be closed by a closure which bursts under the influence of the excess pressure developing with heating, or with a closure which melts with heating.

For carrying out the described method, vessels for accommodating a solid sample substance are provided which can be closed by closures which are destroyed when heated. A conveying device is provided in which a plurality of such vessels can be inserted and by which each of these vessels is consecutively movable into a working position. Further, the device comprises a cover having a carrier gas inlet port and a carrier gas outlet port with the carrier gas inlet port being connectable to a carrier gas source, and means for sealingly placing the cover onto the vessel in working position. A first heating device serves for heating the vessel in working position and the substance contained therein, after the placement of the cover. A body, made of amalgam-generating material with a large surface in a closed system which communicates, on one hand, with the carrier gas outlet port of the cover and, on the other hand, with the measuring vessel of an atomic absorption photometer, serves for the accumulation of the mercury. A second heating device serves for heating the body made of amalgam-generating material such that mercury which is accumulated as amalgam is set free as mercury vapor and is conveyed by carrier gas to the measuring vessel.

The conveying device can be a turntable.

It is advantageous when the first heating device is a lamp serving as heat radiation source, the radiation of which is collected by a reflector at the location of the vessel in the working position.

An embodiment of the invention will now be described in greater detail with reference to the accompanying drawing.

BRIEF DESCRIPTION OF THE DRAWING

The drawing is a schematic illustration and shows a turntable as conveying device for supplying vessels to a working position, a cover which can be placed onto the vessels, a heating device for heating the vessels in order to expel the mercury, a device for accumulating the mercury, a heating device for setting the mercury free again, and a measuring vessel.

PREFERRED EMBODIMENT OF THE INVENTION

Numeral 10 designates a vessel which contains a solid substance 12 which shall be analyzed on mercury. The vessel 10 is closed by a closure 14. The closure 14 is already directly provided after the sample taking. So, it is ensured that no mercury can volatilize from the substance before the analysis or during the sample processing. A plurality of such vessels 10 is arranged in a conveying device 16 designed as a turntable. By the conveying device 16, the vessels 10 are consecutively brought into a working position, which is illustrated on the left hand side of the FIGURE.

In this working position, a cover 18 can be sealingly placed onto the vessel 10. The cover is provided above the closure 14. The closure 14 is a relatively thin membrane which is tentered over the rim of the vessel 10. The cover 18 is placed with a seal 20 on the rim of the vessel. This is accomplished with a lifting device 22 which is here illustrated as a pneumatic cylinder. The cover comprises a carrier gas inlet port 24 and a carrier gas outlet port 26. In operation, the carrier gas inlet port 24 is connected to a carrier gas source.

The vessel 10 in its working position can be heated by a first heating device 28. The heating device 28 comprises a lamp 30 as heat radiation source and a reflector 32. By the reflector, the heat radiation is collected on the vessel 10. Thereby, the substance 12 in the vessel 10 is heated to such high temperatures that the mercury is expelled from the substance and appears as mercury vapor.

By the pressure increase in the vessel 10, which occurs due to heating, the closure 14 bursts. The closure can also be made of a material which melts when the substance 12 and the vessel 10 are heated. In practice, both approaches are effective. In any case, communication between the interior of the housing 10 and the cavity of the cover is accomplished. The carrier gas flow which is supplied through the carrier gas inlet port 24 carries off the mercury vapor, which developed from the substance, through the carrier gas outlet port 26.

The carrier gas and mercury vapor flow passes through a washing bottle 34 with NaOH and a washing bottle 36 with water and, subsequently, through a drying tube 38. The gas flow thus cleaned and dried flows through a gold net 42 arranged in a tube 40. The gold is an amalgam-generating material. The net forms a body with a large surface. The mercury vapor forms an amalgam with the gold and is thus accumulated at the gold net 42. The amount of the wholly accumulated amalgam corresponds to the amount of the mercury in the substance 12 enclosed within the vessel 10. That amount is independent from how fast the mercury is set free from the substance.

After all the mercury has accumulated as amalgam at the gold net 42, the tube 40 and the gold net 42 are heated by a second heating device 44, which is here illustrated as a flame. The amalgam is decomposed and the mercury is again set free as mercury vapor. This is now made in a reproducible manner independent from the type of the substance 12. The mercury vapor is conveyed by the carrier gas flow into a measuring vessel 46 and is determined by the atomic absorption spectral photometry.

After the analysis is conducted, the cover 18 is lifted from the vessel 10 by the lifting device 22. The turntable is moved on by one step so that the next, still closed vessel 10 can be moved into the working position. Then, the described procedure is repeated.

The described arrangement offers the advantage that the sample is introduced into the analyzing apparatus in its original condition without further treatment. Up to this moment, the sample is enclosed within the vessel such that no mercury can volatilize and the sample is also not exposed to any environmental influences. The substance which is to be analyzed can already be filled into the vessel 10 at the location of sample taking which is far from the location of the analysis. The analyses can be automated in the described way.

I claim:

1. A method for analyzing a solid substance comprising mercury by measuring the atomic absorption with the method steps:

enclosing the solid substance within at least one sample vessel, with a closure, heating the at least one sample vessel to vaporize the mercury in the solid substance and destroy the closure to expel the vaporized mercury from the at least one sample vessel, conveying the generated mercury vapor with a carrier gas flow over a body having a large surface made of an amalgamgenerating material, so that the mercury vapor bonds and is accumulated as amalgam on the surface of this body, subsequently heating the body in order to vaporize the mercury accumulated as amalgam again, and conveying the mercury vapor from the amalgam by a carrier gas flow into a measuring vessel of an atomic absorption spectrometer; and analyzing the vapor for the concentration of mercury.

2. The method as set forth in claim 1, further comprising the steps of:

placing a sealing cover about the closure on the at least one sample vessel through which cover a carrier gas flow may be supplied or carried off, subsequently transporting the generated mercury vapor over the amalgam-generating body by the carrier gas.

3. The method as set forth in claim 2, wherein the heating of the solid substance is made by focusing a radiation source onto the substance.

4. The method as set forth in claim 2, wherein said at least one sample vessel comprises a plurality of sample vessels and further comprising the step of conveying the vessels consecutively and automatically to a location where the placement of the cover and the heating is made.

5. The method as set forth in claim 1, wherein said heating of the at least one sample vessel causes the closure to burst under the influence of the excess pressure developing in the at least one sample vessel when heated.

6. The method as set forth in claim 1, wherein said heating of the at least one sample vessel causes the closure to melt.

7. An apparatus for analyzing solid substances on mercury by atomic absorption, comprising a plurality of vessels for accommodating a solid sample substance, each of said vessels equipped with a closure means which will be destroyed when a corresponding one of said vessels is heated, a conveying means for conveying said plurality of vessels, one after the other, into a working position, a cover having a carrier gas inlet port and a carrier gas outlet port, the carrier gas inlet port being arranged to be connected to a carrier gas source, means for sealingly placing the cover on one of the respective vessels which is in the working position, first heating means for heating one of said vessels when in the working position and the substance contained therein after the placement of the cover, a body consisting essentially of amalgam-generating material with a large surface disposed in a closed system flow communication means connected to the carrier outlet port of the cover, and to a measuring vessel of an atomic absorption photometer, and a second heating means for heating said body such that mercury, which has been accumulated as amalgam on said surface of said body, is vaporized as mercury vapor and is conveyed by the carrier as to the measuring vessel.

8. An apparatus as set forth in claim 7, wherein the closure means of the vessels comprise membranes which burst under the influence of the excess pressure developed within the vessel when heated.

9. An apparatus as set forth in claim 7, wherein the closure means of the vessels are made of a material which melts when heated.

10. An apparatus as set forth in claim 9, wherein the conveying means is a turntable.

11. An apparatus as set forth in claim 10, wherein the first heating means comprises a lamp and reflector serving as a heat radiation source.

* * * * *

UNITED STATES PATENT AND TRADEMARK OFFICE
CERTIFICATE OF CORRECTION

PATENT NO. : 5,045,476

DATED : September 3, 1991

INVENTOR(S) : Bernahard Huber

It is certified that error appears in the above-identified patent and that said Letters Patent is hereby corrected as shown below:

Column 2, line 41, after driven insert --off from the water and--.

Column 6, line 67, change "as" to --gas--.

Signed and Sealed this

Ninth Day of March, 1993

*Attest:*

STEPHEN G. KUNIN

*Attesting Officer*     *Acting Commissioner of Patents and Trademarks*